United States Patent [19]

Rose et al.

[11] Patent Number: 5,680,319
[45] Date of Patent: Oct. 21, 1997

[54] HIERARCHICAL PROTEIN FOLDING PREDICTION

[75] Inventors: George D. Rose, Glen Arm; Raigopal Srinivasan, Baltimore, both of Md.

[73] Assignee: The Johns Hopkins University School of Medicine, Baltimore, Md.

[21] Appl. No.: 450,390

[22] Filed: May 25, 1995

[51] Int. Cl.$^6$ .................................................. G06F 17/50
[52] U.S. Cl. .................................................. 364/496; 364/578
[58] Field of Search .................................. 364/496, 499, 364/497, 578; 436/86, 89

[56] References Cited

U.S. PATENT DOCUMENTS

| | | | |
|---|---|---|---|
| 4,855,931 | 8/1989 | Saunders | 364/499 |
| 5,241,470 | 8/1993 | Lee et al. | 364/413.15 |
| 5,260,882 | 11/1993 | Blanco et al. | 364/499 |
| 5,265,030 | 11/1993 | Skolnick et al. | 364/496 |

*Primary Examiner*—Emanuel T. Voeltz
*Assistant Examiner*—M. Kemper
*Attorney, Agent, or Firm*—Fish & Richardson P.C.

[57] ABSTRACT

A computer-assisted method for predicting the three-dimensional structure of a protein fragment from its amino acid sequence. A hierarchic procedure ascends the folding hierarchy in discrete stages with concomitant accretion of structure. The protein fragment may be represented by a simplified geometry and folds under the influence of a primitive energy function.

11 Claims, 17 Drawing Sheets

Ser

Asp, Asn

Glu, Gln

Arg, Lys

Leu

Met

HIERARCHICAL PROTEIN FOLDING PREDICTION

BACKGROUND OF THE INVENTION

1. Field of the Invention

This invention relates to a computer-assisted method for determining the three-dimensional structure of proteins.

2. Description of Related Art

Proteins (or polypeptides) are linear polymers of amino acids. The polymerization reaction which produces a protein results in the loss of one molecule of water from each amino acid, and hence proteins are often said to be composed of amino acid "residues." Natural protein molecules may contain as many as 20 different types of amino acid residues, each of which contains a distinctive side chain. The particular linear sequence of amino acid residues in a protein defines the primary sequence, or primary structure, of the protein. The primary structure of a protein can be determined with relative ease using known methods.

Proteins fold into a three-dimensional structure. The folding is determined by the sequence of amino acids and by the protein's environment. Examination of the three-dimensional structure of numerous natural proteins has revealed a number of recurring patterns. Patterns known as alpha helices, parallel beta sheets, anti-parallel beta sheets, and coils are the most common observed. A description of such protein patterns is provided by Dickerson, R. E., et al. in *The Structure and Action of Proteins*, W. A. Benjamin, Inc. Calif. (1969). The assignment of each amino acid residue to one of these patterns defines the secondary structure of the protein. The combination of the helices, sheets, turns, and coils of a protein's secondary structure produce the folded three-dimensional, or tertiary, structure of the protein.

The three-dimensional structure of proteins has been determined in a number of ways. Perhaps the best known way of determining protein structure involves the use of the technique of x-ray crystallography. A general review of this technique can be found in *Physical Bio-chemistry*, Van Holde, K. E. (Prentice-Hall, N.J. 1971), pp. 221–239, or in *Physical Chemistry with Applications to the Life Sciences*, D. Eisenberg & D. C. Crothers (Benjamin Cummings, Menlo Park 1979). Using this technique, it is possible to elucidate three-dimensional structure with good precision. Additionally, protein structure may be determined through the use of the techniques of neutron diffraction, or by nuclear magnetic resonance (NMR). See, e.g., *Physical Chemistry*, 4th Ed. Moore, W. J. (Prentice-Hall, N.J. 1972) and *NMR of Proteins and Nucleic Acids*, K. Wüthrich (Wiley-Interscience, N.Y. 1986). However, such techniques are extremely time consuming, often requiring months to derive the three-dimensional structure of a single protein.

The biological properties of proteins depend directly on the protein's three-dimensional (3D) conformation. The conformation determines the activity of enzymes, the capacity and specificity of binding proteins, and the structural attributes of receptor molecules. Because the three-dimensional structure of a protein molecule is so significant, it has long been recognized that a means for readily determining a protein's three-dimensional structure from its known amino acid sequence would be highly desirable. However, it has proved extremely difficult to make such a determination. One difficulty is that each protein has an astronomical number of possible conformations (about $10^{16}$ for a small protein of 100 residues; see K. A. Dill, *Biochemistry*, 24, 1501–1509, 1985), and there has been no reliable method for picking the one conformation stable in aqueous solution. A second difficulty is that there are no accurate and reliable force laws for the interaction of one part of a protein with another part and with water. These and other factors have contributed to the enormous complexity of determining the most probable relative location of each residue in a known protein sequence.

The protein folding problem, the problem of determining a protein's three-dimensional tertiary structure from its amino acid sequence, was first formulated more than half a century ago. Early observations and later experiments have lead to the contemporary view that protein conformation is determined solely by the amino acid sequence and that there exists a unique native conformation in which residues distant in sequence but proximate in space engender a close-packed core enriched in hydrophobic residues. As a result of the revolution in molecular biology, the number of known protein sequences is about 50 times greater than the number of known three-dimensional protein structures. This disparity hinders progress in many areas of biochemistry because a protein sequence has little meaning outside the context of the three-dimensional structure.

Current approaches to solving the folding problem can be classified into direct methods and template-based methods. Direct methods seek the native fold as a low(est) energy point in some suitably defined hyperspace of conformational possibilities. Template-based methods compare a sequence of unknown conformation against a library of solved structures and, using a suitable metric, score good matches as likely folds. Many papers on such approaches to three-dimensional structure have appeared in recent years. However, none of the approaches have been particularly successful.

Consequently, there has been a long-felt need for a method for predicting the fold of a protein from its amino acid sequence alone.

SUMMARY OF THE INVENTION

Disclosed is a direct prediction method that capitalizes on the observation that globular proteins are organized as a structural hierarchy. Consistent with hierarchic folding, protein secondary structure is codified into only four categories—helix, sheet, turns, and loops. A complex fold is decomposed into the elements contained within these categories, together with their superstructures.

The method described here operates on a polypeptide chain of defined sequence, preferably starting in a fully extended conformation. No other input information is required. Using idealized geometry and a highly simplified energy function, the chain is folded in hierarchic stages, with concomitant accretion of structure at each step. The method predicts both secondary and supersecondary structure effectively.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 8b is a block diagram of a processor of the computer of FIG. 8a.

Like reference numbers and designations in the various drawings refer to like elements.

DETAILED DESCRIPTION OF THE INVENTION

Throughout this description, the preferred embodiment and examples shown should be considered as exemplars, rather than limitations on the present invention.

In brief, the protein folding prediction method accumulates favorable protein chain structure within a fixed, sequential interval of allowed interaction, then repeats this process in stages as the interval size increases. At each stage, the chain is allowed to move (protein conformation is allowed to change) at random under the influence of an energy function. Hierarchy is established by recognizing favorable conformations in early stages and constraining them to persist during later stages. The move set was chosen to represent populated regions in $\phi$, $\psi$-space: helix, sheet, and turns. Only three types of interaction are taken into account in the energy function—one repulsive, the other two attractive. Repulsive interactions measure steric overlap; two nonbonded atoms cannot occupy the same space at the same time. Attractive interactions measure hydrogen bonds and the tendency of apolar residues to cluster.

Figure 1:
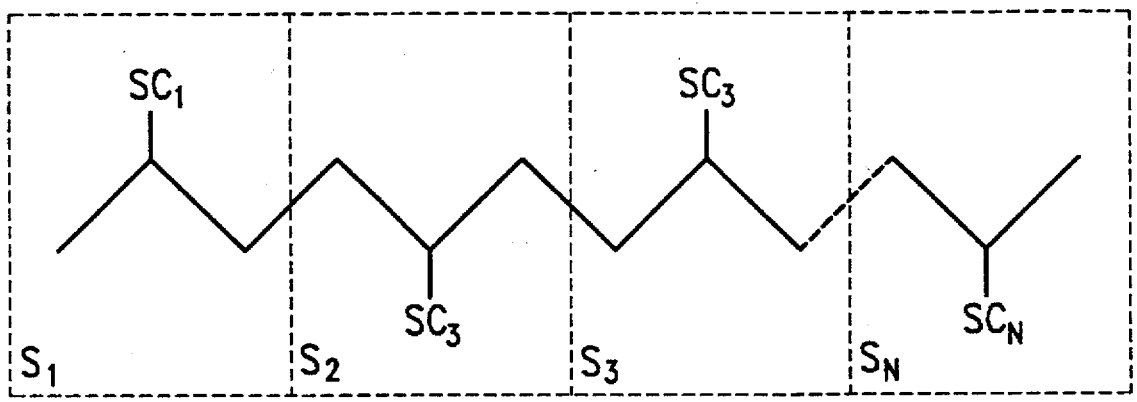
FIG. 1 is a schematic diagram of an amino acid chain.
Figure 8A:
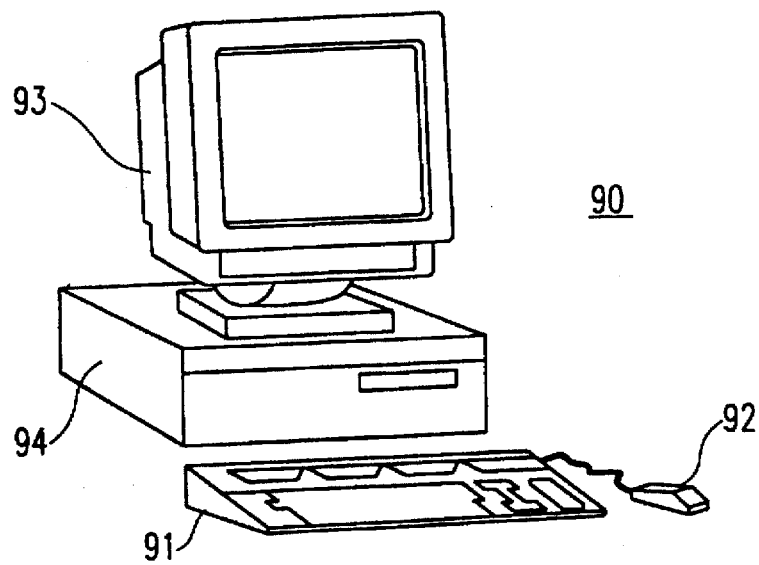
FIG. 8a is a perspective view of a generalized computer suitable for implementing the method.

Turning to FIG. 1, the starting point of a simulation run (an execution of the method on a programmed computer, such is shown in FIG. 8a) is an amino acid sequence, S, where $S=s_1-s_2-s_3- \ldots s_N$, shown schematically, with schematic side chains $sc_1-sc_2-sc_3- \ldots sc_N$. Residues are represented by the indexed, lower case 's', with N residues in the sequence. The method keeps track of two particular chain conformations: (i) the current conformation, C; and (ii) a trial conformation, C*. At the onset, the interaction interval, $\Delta$, is 6 residues in length, and the starting conformation is set to an extended backbone conformation ($\phi=-150°$, $\psi=150°$, $\omega=180°$), with the side chains pointed away from the main chain ($\chi=180°$).

A simulation run proceeds as follows. Progressing sequentially (one residue at a time) from the N-terminus to the C-terminus of S, three consecutive residues are moved simultaneously (as will be described) to generate C*, a new trial conformation. C* is rejected if any two atoms in the entire sequence overlap. Otherwise, the energy function U of C* is computed by summing interactions between all residues in S that are separated in sequence by no more than the current interaction interval, $\Delta$. C* is rejected if a random number between 0 and 1 is less than the Boltzmann-weighted energy, $e^{-\beta \Delta E/T}$, where $\beta=2$ and $T=1$ and $\Delta E=U(C^*)-U(C)$. (The $\beta$ is a factor for the Monte-Carlo strategy; T is included to show the form of a Boltzmann weighting.) If not rejected, the trial conformation is accepted; i.e., the current conformation, C, is set to C*. A complete progression from the N-terminus to the C-terminus is termed a cycle. For each interaction interval, 6000 cycles are performed, consisting of 1000 equilibration cycles (to avoid biasing the result by the choice of initial conformation) followed by 5000 trial cycles. Equilibration cycles are discarded; the conformations at the end of each trial cycle are retained to form a trial ensemble. Chain segments in the trial ensemble that adopt a persisting conformation throughout an interval are "frozen", i.e., constrained to remain in that conformation during subsequent intervals.

In one implementation of a simulation run, protein monomers have been subdivided into overlapping 50-residue fragments, although the ultimate fragment at the C-terminus is allowed to exceed 50 residues. Each fragment is autonomous. The interval size, $\Delta$, is allowed to grow in 6-residue increments until $\Delta=48$ is attained. However, while 50-residue fragments provide useful results, the method is not limited to operation on 50-residue fragments.

Thus, it should be noted that fragmentation into autonomous 50-residue segments is arbitrary and can result in spurious end-effects for larger values of $\Delta$ because fragment termini can be recruited into non-native intra-fragment interactions when deprived of native interactions with those residues that happen to partition into an adjacent fragment. This problem would not occur within the context of the whole protein. Surprisingly, the problem appears to be infrequent A complete simulation run of the method can be represented diagrammatically as:

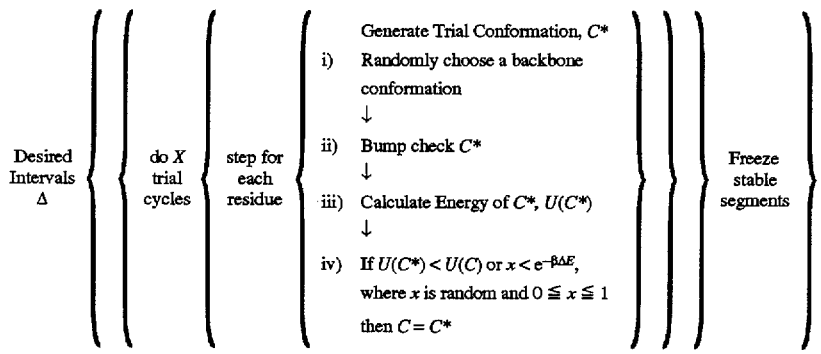

where the innermost brackets surround the inner loop. The energy U of the current conformation will typically decrease over the course of each interval and from each interval to the next. Upon completion, the minimum energy structure among the ensemble of conformations from the final interval is accepted as the predicted conformation.

The energy units used in the calculations, though not entirely arbitrary (see below), are crude, and a Monte Carlo-motivated strategy was employed to permit escape from local energy traps and to assure that the ensemble of conformations generated in the trial cycles will have energies that are Boltzmann distributed. It should be emphasized that the method is authentic Monte Carlo within intervals but not between intervals, because the "freezing" of persisting structure abolishes microscopic reversibility.

Chain conformations are generated by randomly varying backbone and side chain torsion angles $\phi$, $\psi$, $\omega$ and $\chi$. Since the smallest local conformations—a turn of helix or a β-turn—involve several consecutive residues, the "move set" moves the chain three residues at a time, with moves chosen at random from the possibilities listed below. (The terms "move" and "move set" are used to refer to the perturbations to be consistent with conventional usage in describing Monte-Carlo simulations.)

Chain Geometry. The method uses backbone atoms—N, $C_\alpha$, C, O, and $C_\beta$—and the highly simplified side chains illustrated in FIGS. 2a, 2b and 2c. Ideal values of backbone bond lengths and scalar angles are maintained throughout. In the computer program implementation described later, conformations are generated in internal coordinates and then transferred to Cartesian geometry for evaluation.

The Move Set. The Monte-Carlo strategy employs a "smart move set" explicitly designed to overcome conformational entropy. During each cycle, a residue pointer is advanced sequentially from N to C. With the pointer at i (the i-th residue), a new backbone conformation is chosen at random from one of four conformation types:

Helix—three consecutive residues, (i−1, i, i+1), are each set to helical conformation, viz. $\phi=-64\pm15°$, $\psi=-43\pm15°$, $\omega=180\pm10°$.

Strand—three consecutive residues, (i−1, i, i+1), are each set to strand conformation, viz. $\phi=-120\pm30°$, $\psi=120\pm30°$, $\omega=180\pm10°$.

3. Turn—three consecutive residues, (i−1, i, i+1), are each set at random to one of 9 turn types for glycine or proline, or one of 8 turn types for all other residues, viz.

i. Type I followed by left-hand conformation
  residue (i − 1): $\phi = -60 \pm 15°$, $\psi = -30 \pm 15°$, $\omega = 180 \pm 10°$
  residue (i):     $\phi = -90 \pm 15°$, $\psi = 0 \pm 15°$, $\omega = 180 \pm 10°$
  residue (i + 1): $\phi = 90 \pm 15°$, $\psi = 0 \pm 15°$, $\omega = 180 \pm 10°$
ii. Type I followed by left-hand conformation
  residue (i − 1): $\phi = -60 \pm 15°$, $\psi = -30 \pm 15°$, $\omega = 180 \pm 10°$
  residue (i):     $\phi = -90 \pm 15°$, $\psi = 0 \pm 15°$, $\omega = 180 \pm 10°$
  residue (i + 1): $\phi = 90 \pm 15°$, $\psi = 120 \pm 15°$, $\omega = 180 \pm 10°$
iii. Extended conformation followed by Type I
  residue (i − 1): $\phi = -90 \pm 15°$, $\psi = 120 \pm 15°$, $\omega = 180 \pm 10°$
  residue (i):     $\phi = -60 \pm 15°$, $\psi = -30 \pm 15°$, $\omega = 180 \pm 10°$
  residue (i + 1): $\phi = -90 \pm 15°$, $\psi = 0 \pm 15°$, $\omega = 180 \pm 10°$
iv. Type I' followed by extended conformation
  residue (i − 1): $\phi = 60 \pm 15°$, $\psi = 30 \pm 15°$, $\omega = 180 \pm 10°$
  residue (i):     $\phi = 90 \pm 15°$, $\psi = 0 \pm 15°$, $\omega = 180 \pm 10°$
  residue (i + 1): $\phi = 90 \pm 15°$, $\psi = 120 \pm 15°$, $\omega = 180 \pm 10°$
v. Type II followed by extended conformation
  residue (i − 1): $\phi = -60 \pm 15°$, $\psi = 120 \pm 15°$, $\omega = 180 \pm 10°$
  residue (i):     $\phi = 80 \pm 15°$, $\psi = 0 \pm 15°$, $\omega = 180 \pm 10°$
  residue (i + 1): $\phi = -90 \pm 15°$, $\psi = 120 \pm 15°$, $\omega = 180 \pm 10°$ -continued vi. Extended conformation followed by Type II
  residue (i − 1): $\phi = -90 \pm 15°$, $\psi = 120 \pm 15°$, $\omega = 180 \pm 10°$
  residue (i):     $\phi = -60 \pm 15°$, $\psi = 120 \pm 15°$, $\omega = 180 \pm 10°$
  residue (i + 1): $\phi = 80 \pm 15°$, $\psi = 0 \pm 15°$, $\omega = 180 \pm 10°$
vii. Type II' followed by extended conformation
  residue (i − 1): $\phi = 60 \pm 15°$, $\psi = -120 \pm 15°$, $\omega = 180 \pm 10°$
  residue (i):     $\phi = -80 \pm 15°$, $\psi = 0 \pm 15°$, $\omega = 180 \pm 10°$
  residue (i + 1): $\phi = -90 \pm 15°$, $\psi = 120 \pm 15°$, $\omega = 180 \pm 10°$
viii. Type V followed by extended conformation
  residue (i − 1): $\phi = -80 \pm 15°$, $\psi = 80 \pm 15°$, $\omega = 180 \pm 10°$
  residue (i):     $\phi = 80 \pm 15°$, $\psi = -80 \pm 15°$, $\omega = 180 \pm 10°$
  residue (i + 1): $\phi = -90 \pm 15°$, $\psi = 120 \pm 15°$, $\omega = 180 \pm 10°$
ix. Glycine half-turn
  residue (i − 1): $\phi = -100 \pm 15°$, $\psi = -120 \pm 15°$, $\omega = 180 \pm 10°$
  residue (i):     $\phi = 110 \pm 15°$, $\psi = -160 \pm 15°$, $\omega = 180 \pm 10°$
  residue (i + 1): $\phi = -90 \pm 15°$, $\psi = 140 \pm 15°$, $\omega = 180 \pm 10°$
x. Type VI (cis-proline) followed by extended conformation
  residue (i − 1): $\phi = -120 \pm 15°$, $\psi = 120 \pm 15°$, $\omega = 180 \pm 10°$
  residue (i):     $\phi = -70 \pm 15°$, $\psi = 150 \pm 15°$, $\omega = 0 \pm 10°$
  residue (i + 1): $\phi = -90 \pm 15°$, $\psi = 120 \pm 15°$, $\omega = 180 \pm 10°$ 4. Coil—three consecutive residues, (i−1, i, i+1), are each set to have random values of $\phi$ and $\psi$ between −180° and 180°, with $\omega=180\pm10°$. However, if one of the residues is proline, 20% of the time its $\omega$ is set to $0\pm10°$. Also, for glycine $\phi$ is always set to a value between 0° and 180°.

Each side chain has at most one torsion angle which is set to have a random value of $\chi$ between −180° and 180°.

The Energy Function. The energy function U is extremely simple and includes just three components, which are summed: (i) a scaled contact energy with both attractive and repulsive terms, (ii) a primitive hydrogen bonding potential, and (iii) a main chain torsional potential that helps "chase" the backbone away from values of $\phi>0$ for residues other than glycine.

The repulsive component of the contact energy (i.e., steric repulsion) is the only accurately represented term in the energy function. It is implemented by rejecting conformations in which the interatomic distance between any two atoms is less than the sum of their respective van der Waals radii, which are taken as 1.7 Å for carbon and sulfur, 1.45 Å for nitrogen, and 1.28 Å for oxygen. All pairwise interactions are evaluated except those involving carbonyl carbons, which are ignored. In addition, atoms connected covalently or by scalar angles (i.e., 1–3 interactions) or torsion angles (i.e., 1–4 interactions) are not evaluated.

Figure 2A:
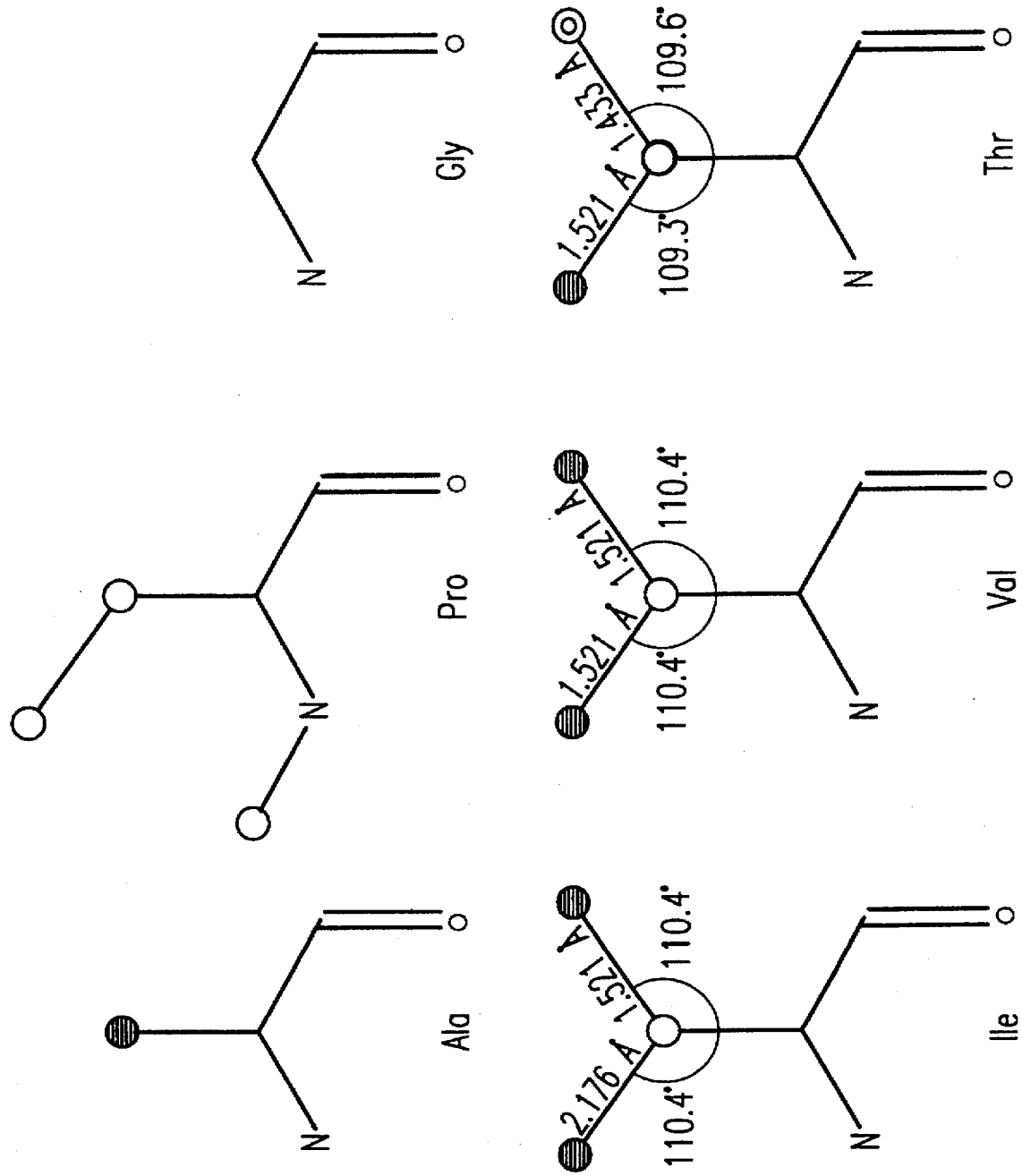
FIGS. 2a, 2b, and 2c schematically illustrate the simplified side chains used in energy calculations and show their pertinent parameters.
Figure 2B:
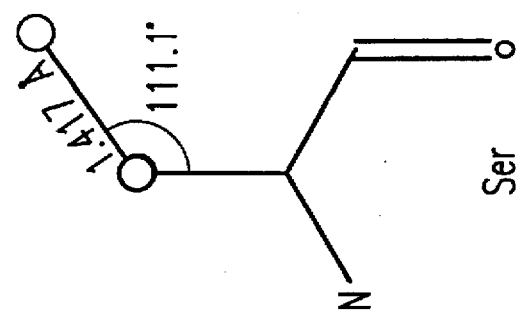
Figure 2B:
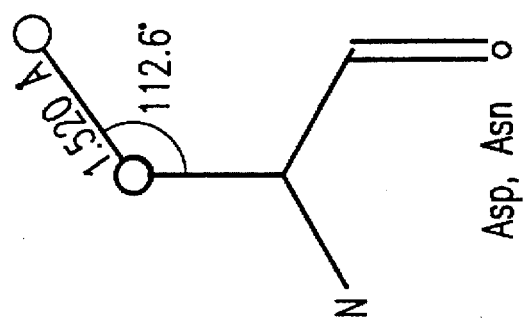
Figure 2B:
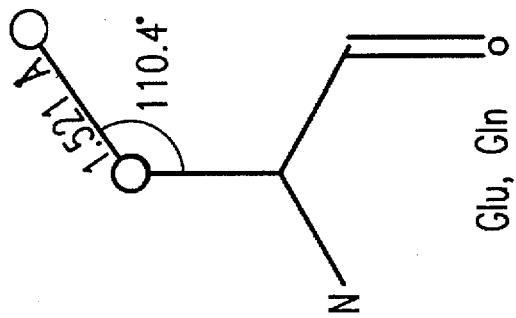
Figure 2B:
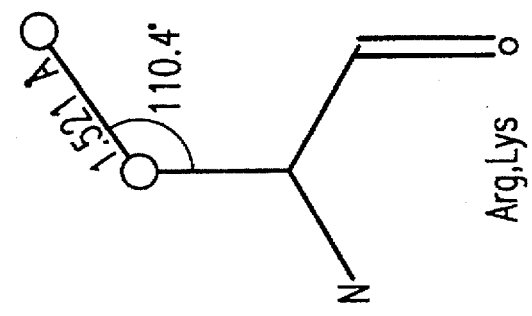
Figure 2B:
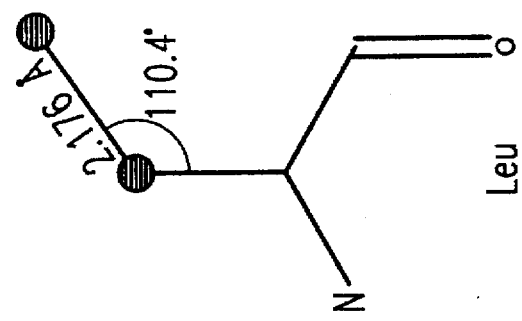
Figure 2B:
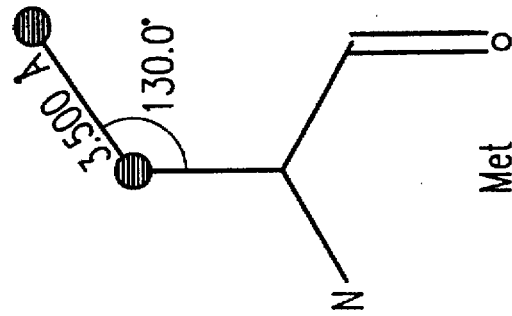
Figure 2C:
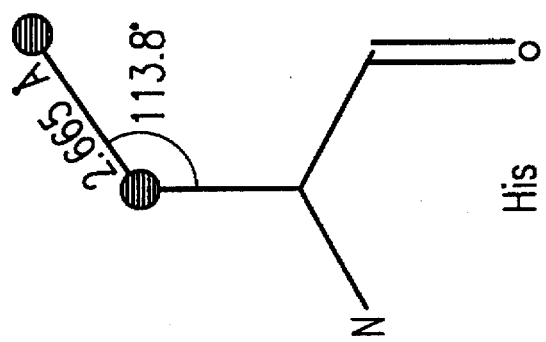
Figure 2C:
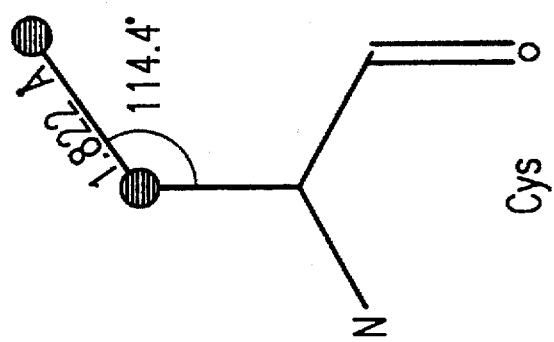
Figure 2C:
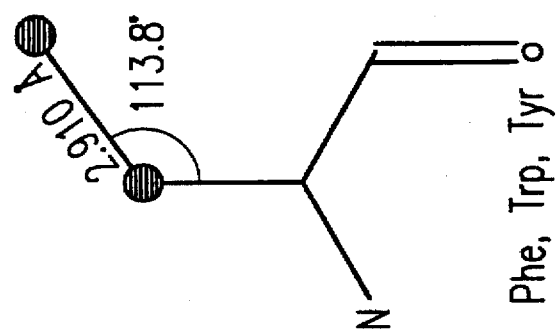

The simple attractive term is applied between the side chain pseudo-atoms illustrated and defined in FIGS. 2a, 2b, and 2c, where the atomic structure of each simplified side chain is shown. Each side chain has at most one torsion angle ($\chi$-angle). All side chain atoms occupy space and contribute to excluded volume. Atoms designated by opaque circles can participate in hydrophobic interactions. Atoms designated by shaded circles can serve as acceptors for backbone-to-side chain hydrogen bonds. Side chain radii have been assigned as follows (in Å): all β-carbons are 2.0. $C_\gamma^1$ and $C_\gamma^2$ of Ile and Val, $C_\gamma^2$ of Thr, and $S_\gamma$ of Cys are also 2.0. Other $C_\gamma$'s, in order of increasing size, are: 2.50 for His; 3.00 for Met and Leu; and 3.25 for Phe, Tyr, and Trp.

For residues i and j, the pairwise distance, $d_{ij}$, between the two pseudo-atom interaction sites, $C_i$ and $C_j$, is measured and assigned a maximal contact energy of 2 units when both i and j are hydrophobic, 1 unit when either i or j is hydrophobic and the other amphipathic, and 0 when neither i nor j is hydrophobic. As shown in FIGS. 2a, 2b, and 2c, the γ-position of side chains can be represented by either one or two pseudo-atoms. The maximal contact energy associated with a hydrophobic residue is one unit, which is split into two half-unit contributions in hydrophobic residues with two γ-pseudo-atoms. Hydrophobic residues include: Cys, Ile, Leu, Met, Phe, Trp and Val. Amphipathic residues include: Ala, His, Thr and Tyr. The energy units are arbitrary, of course, but are motivated by the consideration that, on average, all hydrophobic residues bury approximately the same fraction of their available hydrophobic surface.

This attractive term is scaled by distance, like a potential. The value is assigned to be maximal for $C_i$–$C_j$ distances less than or equal to $\sigma_{ij}$, the sum of the respective assigned radii of the pseudo-atoms, which are shown in FIGS. 2a, 2b, and 2c, and it diminishes to 0 beyond $\sigma_{ij}+1.4$ (Å). In the interval [$\sigma_{ij}$, $\sigma_{ij}+1.4$ (Å)], the contact energy is calculated as $$=\text{maximum contact energy}\times\{1.0-(d_{ij}^2-\sigma_{ij}^2)/((\sigma_{ij}+1.4)^2-\sigma_{ij}^2)\},$$

where the maximum contact energy is as set forth in the preceding paragraph.

The second component of the energy function is primitive hydrogen bonding potential. Both backbone-to-backbone and backbone-to-side chain hydrogen bonds are allowed within the current Δ-interval. To realize a backbone-to-backbone H-bond, an N . . . O pair must be separated by at least one-residue in sequence and no more than 3.5 Å in space. Also, the out-of-plan dihedral angle between the oxygen and the peptide plane of the nitrogen (C-N-$C_\alpha$) must not exceed 40°. If these criteria are satisfied, an H-bond energy of 0.5 units is assigned if Δ≦12 and 1.0 units if Δ>12.

Backbone-to-side chain hydrogen bonds are allowed between a backbone nitrogen (at residue i), and a side chain acceptor situated at the β-carbon (at residue j). Only short range H-bonds are allowed. For Asn, Asp, Thr and Ser, short range is defined as i−4≦j≦i+4, i≠j. For Gln and Glu, short range is defined as i−4≦j≦i−2. In globular proteins, most backbone-to-side chain hydrogen bonds are found within these intervals. Since our residues lack complete side chains, the $C_\beta$ is used in lieu of the actual acceptor atom. The allowed out-of-plane dihedral angle may not exceed 40° (as above), and the $C_\beta$ to nitrogen distance may not exceed 5 Å. An H-bond energy of 1.0 unit is assigned when these criteria are satisfied.

The third component of the energy function, a main chain torsion potential, is imposed to "chase" residues (except glycine) away from the right side of the φ, ψ-map (i.e., φ>0°). Specifically, a residue with φ>0° is penalized 1.0 units, unless it is Gly. In this latter case, the residue is rewarded 2.0 units if 0°≦φ≦150°.

Hierarchic Accretion. Hierarchy is realized by analyzing chain segments at the end of each interval, i.e., at the end of all cycles for a particular value of Δ. Structurally persisting segments—those that have adopted a preferred conformation throughout the interval—are then constrained to retain this conformation in subsequent intervals. Specifically, continuous 3-residue segments are constrained whenever two conditions are satisfied: (i) during an interval, the segment is found in the same region of φ, ψ-space (helix, extended, or the same turn type) more than 70% of the time, and (ii) in this preferred conformation, the segment can realize a hydrophobic contact, i.e., a hydrophobic residue either within or immediately adjacent to the segment maintains a contact with another such residue. When so constrained, the segment, though "frozen", continues to sample other φ, ψ values within its preferred region. Longer persisting segments—ranging from helices or β-strands to supersecondary structure—become frozen as the concatenation of consecutive smaller frozen segments. (The 70% threshold for accepting segments is a conservative value used in one implementation; however, other and substantially smaller values may be used.)

Figure 7A:
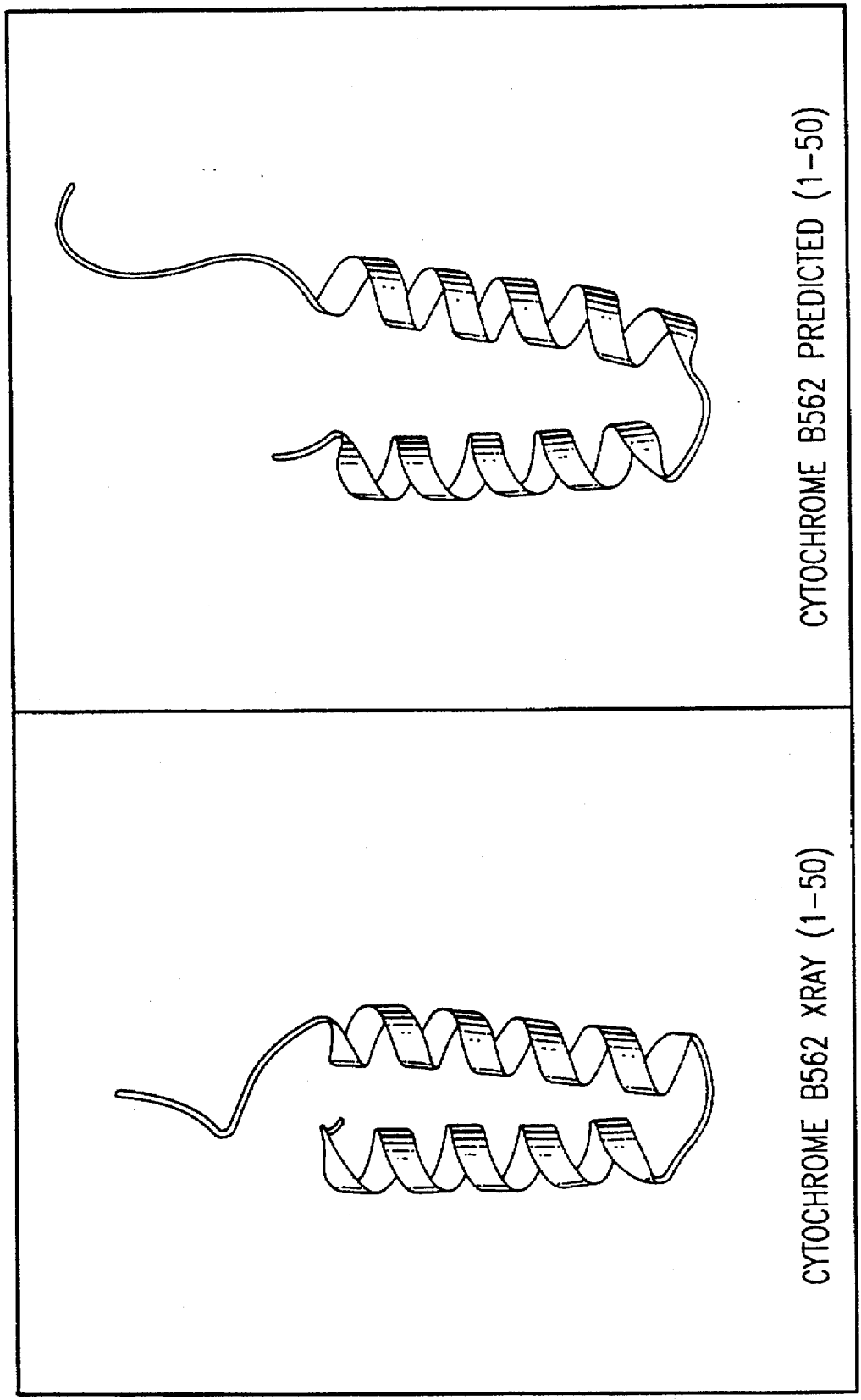
FIGS. 7a, 7b, and 7c show a Molscript representation of a predicted folding of cytochrome $b_{562}$ calculated by an implementation of the method.
Figure 7B:
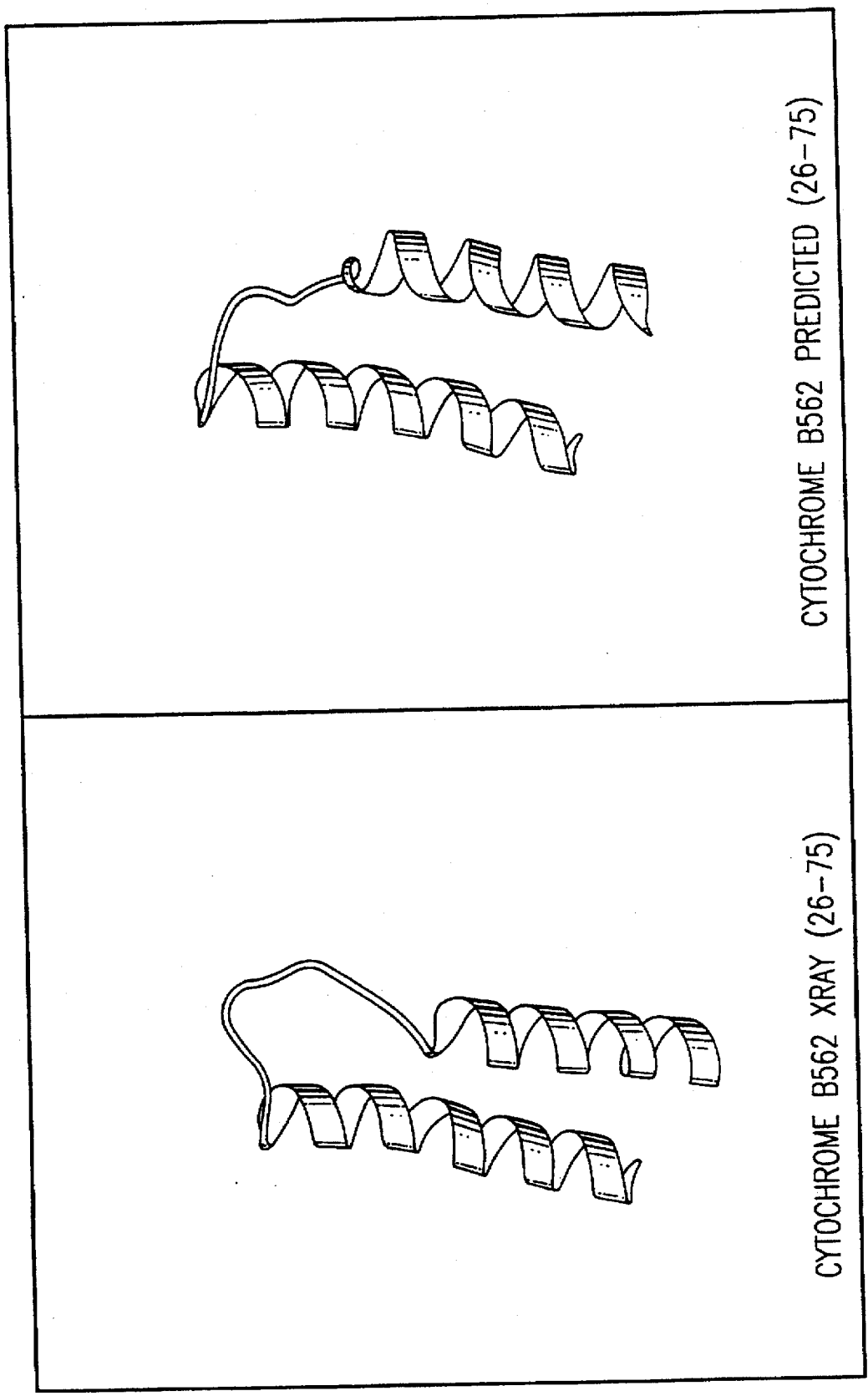
Figure 7C:
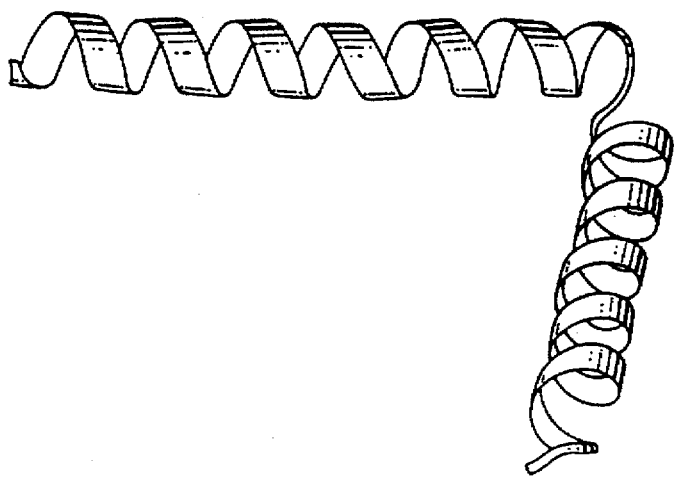
Figure 7C:
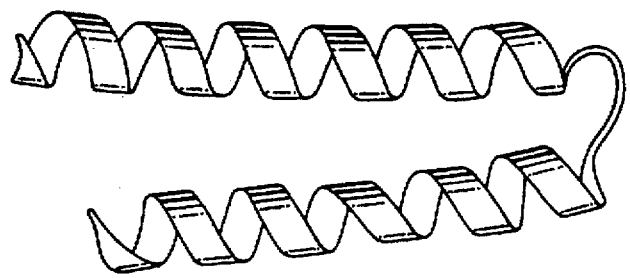

Example Result. Turning to FIGS. 7a–7f, a simulation run on the residue sequence of cytochrome $b_{562}$, a 4-helix bundle protein, shows successful operation of the method on the apoprotein used in the simulation. This series of figures compares the predicted structure with an experimentally determined structure. A Molscript representation of the result is shown in FIGS. 7a–7c. The structure of cytochrome $b_{562}$ has been solved to 1.4 Å resolution. The structure of the apoprotein has been determined by NMR, where it was found that the C-terminal helix is largely unwound. A sole hydrophobic residue anchors this fourth helix to the remainder of the molecule, with an energy of association that is correspondingly small.

Secondary structure and conformationally constrained segments are listed in following table, which compares x-ray against predicted secondary structure for cytochrome $b_{562}$

| Structure | X-ray | Prediction |
|---|---|---|
| helix | 3–19 | 3–18 |
| helix | 23–41 | 24–41 |
| helix | 56–79 | 56–81 |
| helix | 84–104 | 84–104 |
| turn | 80–82 | 80–82 |

The secondary structure possibilities include helix, strand, and hydrogen-bonded turn. Recognition of each category was based solely on dihedral angles: helix is defined as three or more residues with φ=−60±20°; ψ=−40±20°; strand is defined as three or more residues where φ>−80°; ψ<80°; and turns are defined above (under the heading "The Move Set"). The x-ray column shows residues that satisfy the given secondary structure definition in the x-ray structure. The prediction column shows residues that satisfy the given secondary structure definition in the predicted structure.

For the cytochrome $b_{562}$ simulation, the following list shows the segments that were conformationally constrained based on criteria specified above for the process of hierarchic accretion.

Interval=6: 3–7, 7–10, 10–14, 26–33
Interval=18: 34–38, 58–76

As shown on FIG. 7c, helix 4 does not associate with the other three helices in our predicted structure for a reason that appears to be related to its behavior in the NMR-determined apoprotein: insufficient hydrophobic surface is available to promote association. As a result, helices 1–3 twist to each other to optimize their mutual interaction, as shown in FIGS. 7a–7c.

Figure 7D:
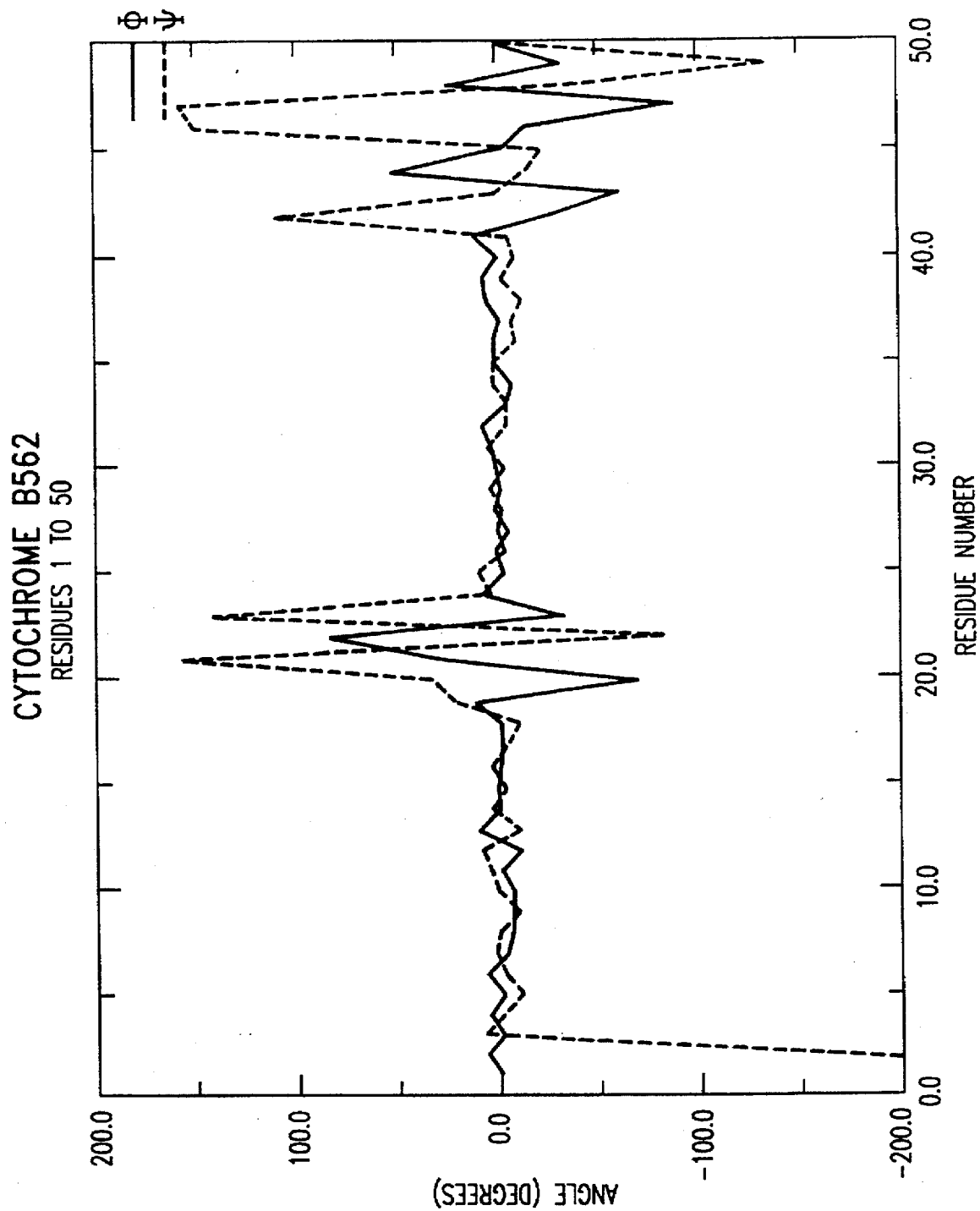
FIGS. 7d, 7e, and 7f are difference dihedral angle plots of the protein fragment conformation shown in FIGS. 7a, 7b, and 7c, respectively, compared to X-ray diffraction conformation.
Figure 7E:
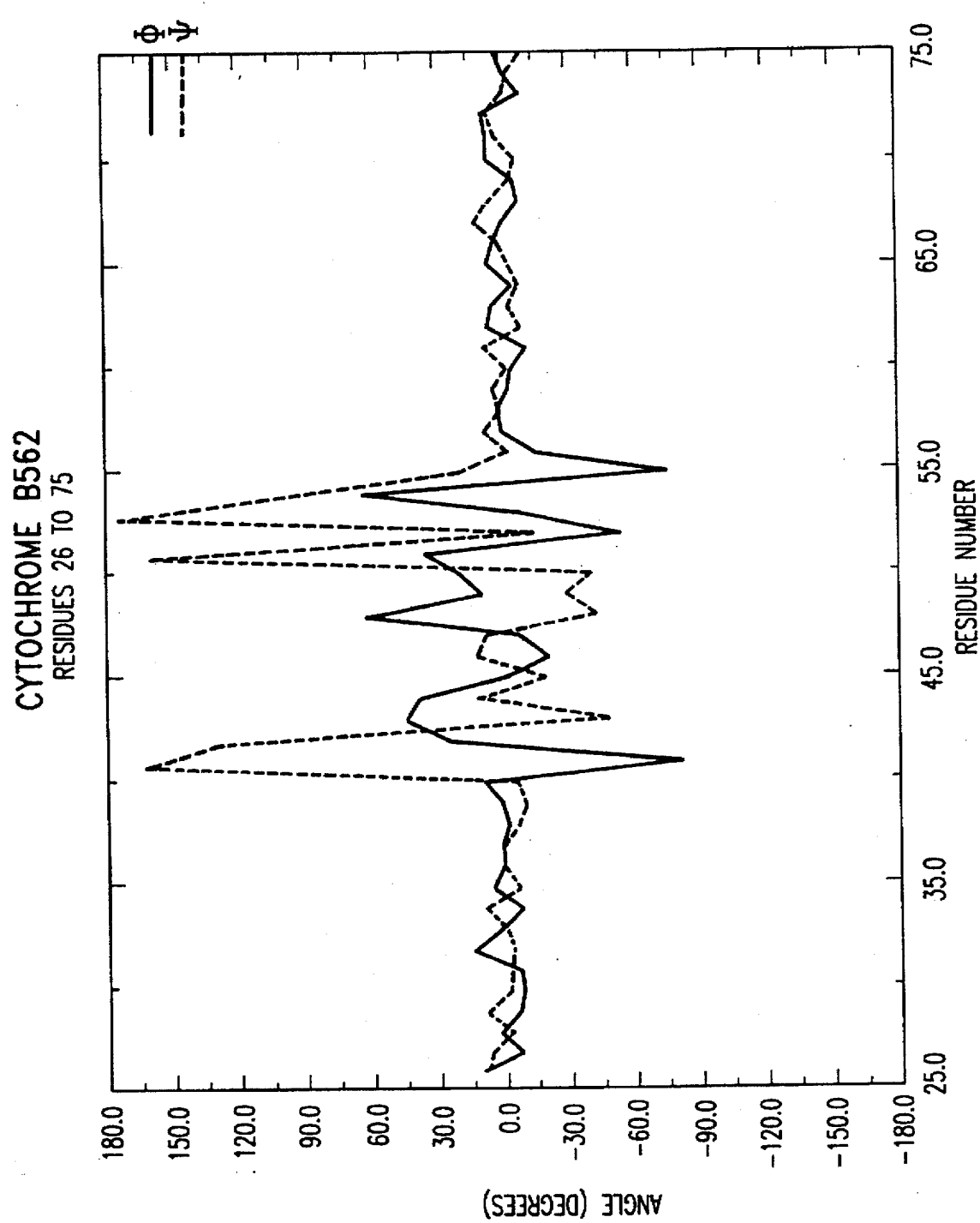
Figure 7F:
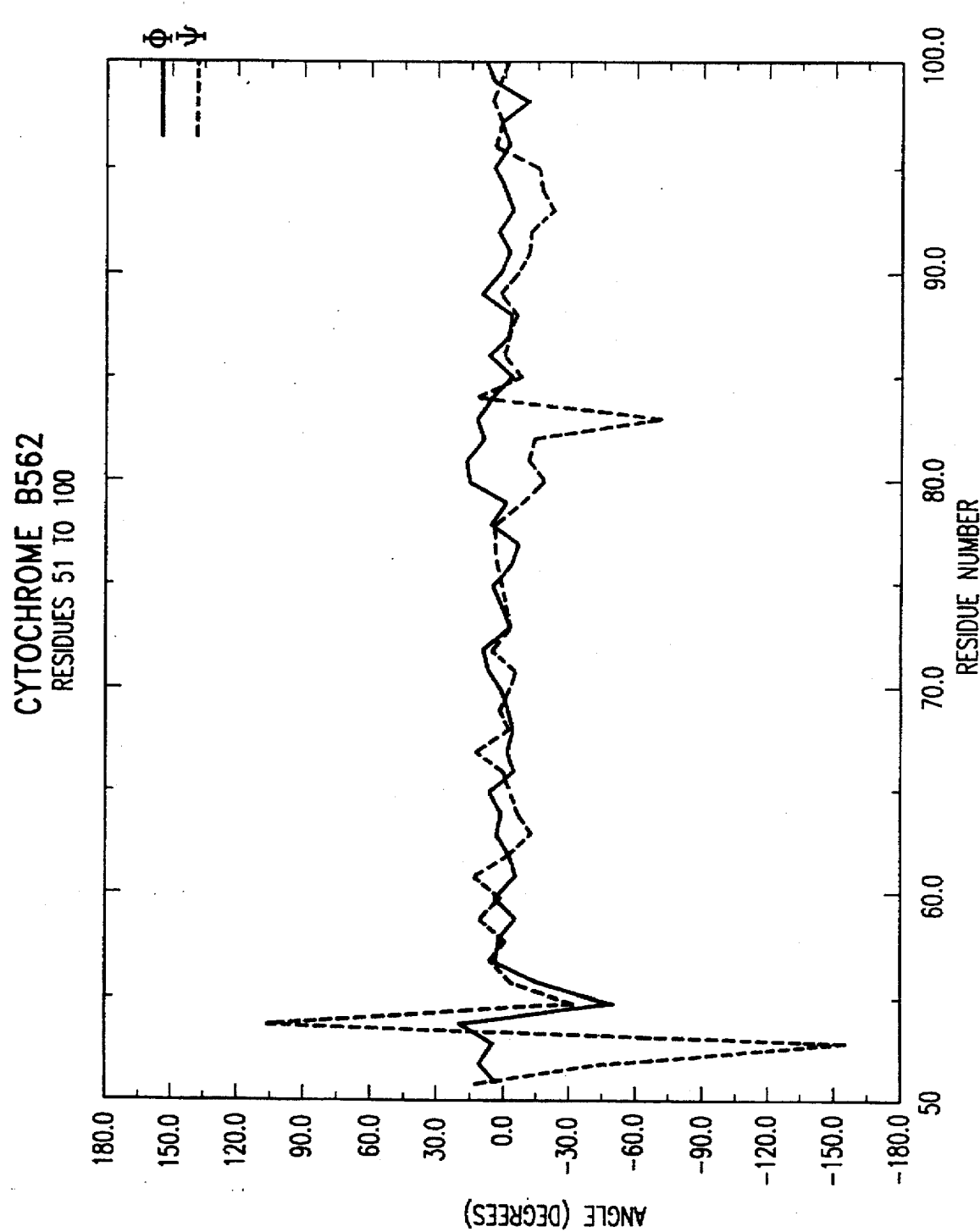

FIGS. 7d–7f show difference dihedral angle plots for the fragments shown in FIGS. 7a–7c, respectively. The difference dihedral angle plots graph both $\phi_{x-ray}(i)-\phi_{predicted}(i)$ (as a solid line) and $\psi_{x-ray}(i)-\psi_{predicted}(i)$ (as a broken line), for every residue i. These plots provide a better comparison than the subjective visual assessment of error in Molscript-rendered fragments, where the eye is easily confounded by small changes in orientation and perceived differences tend to accumulate in a non-linear way. The difference dihedral angle plots provide two figures-of-merit per residue, from which it is apparent that, residue-by-residue, the x-ray and predicted structures are in close agreement in most cases.

Figure 3:
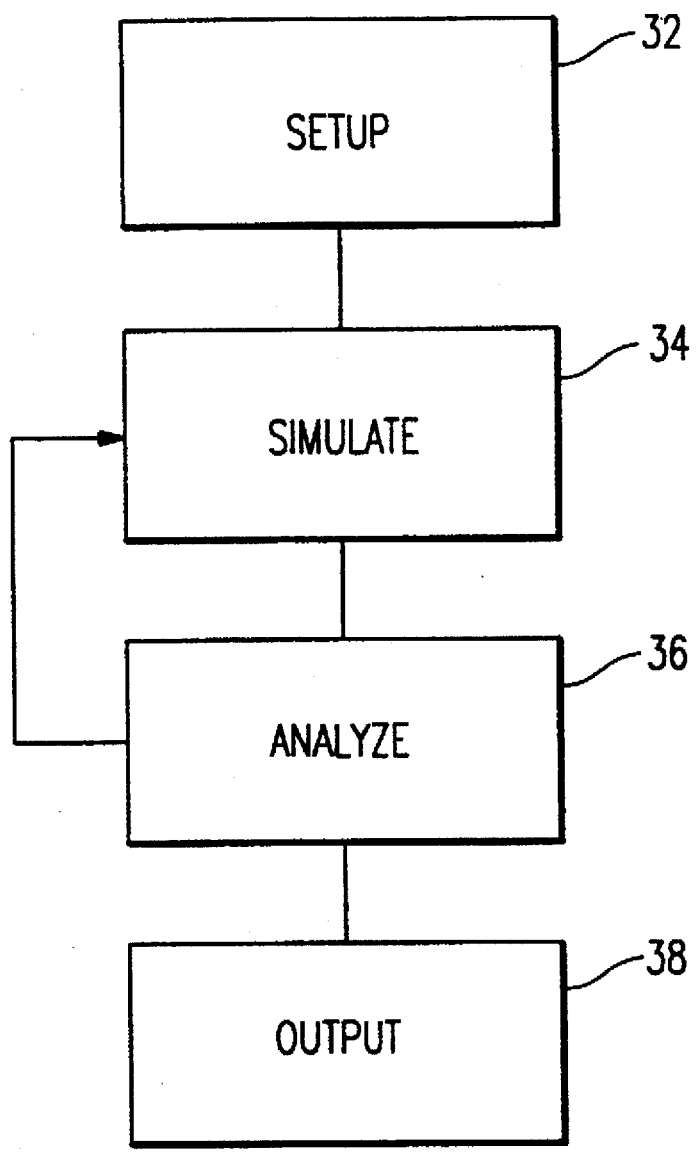
FIG. 3 is a top-level flow chart of an implementation of the method.

Preferred Computer Implementation. Turning to FIG. 3, a flowchart shows the basic steps of the method. An initial setup step 32 sets parameters for a simulation run on a protein chain. Simulate step 34 performs a set of cycles for an interval Δ, and analyze step 36 marks selected parts of the chain as frozen.

Figure 4A:
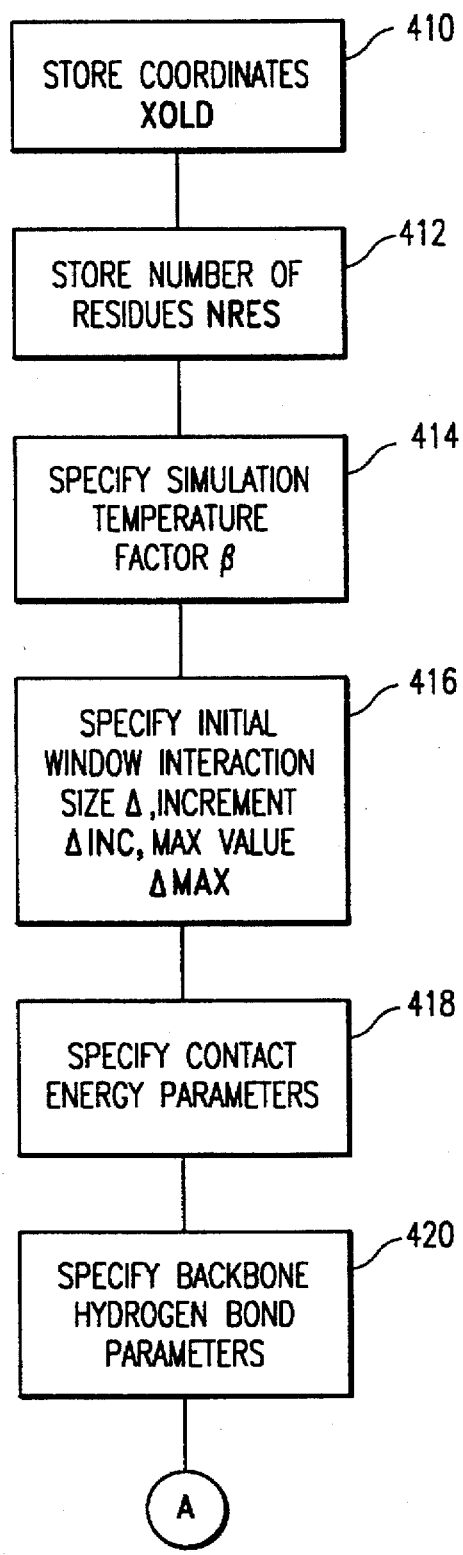
FIGS. 4a and 4b are a block diagram flow chart of a basic setup step of an implementation of the method.
Figure 4B:
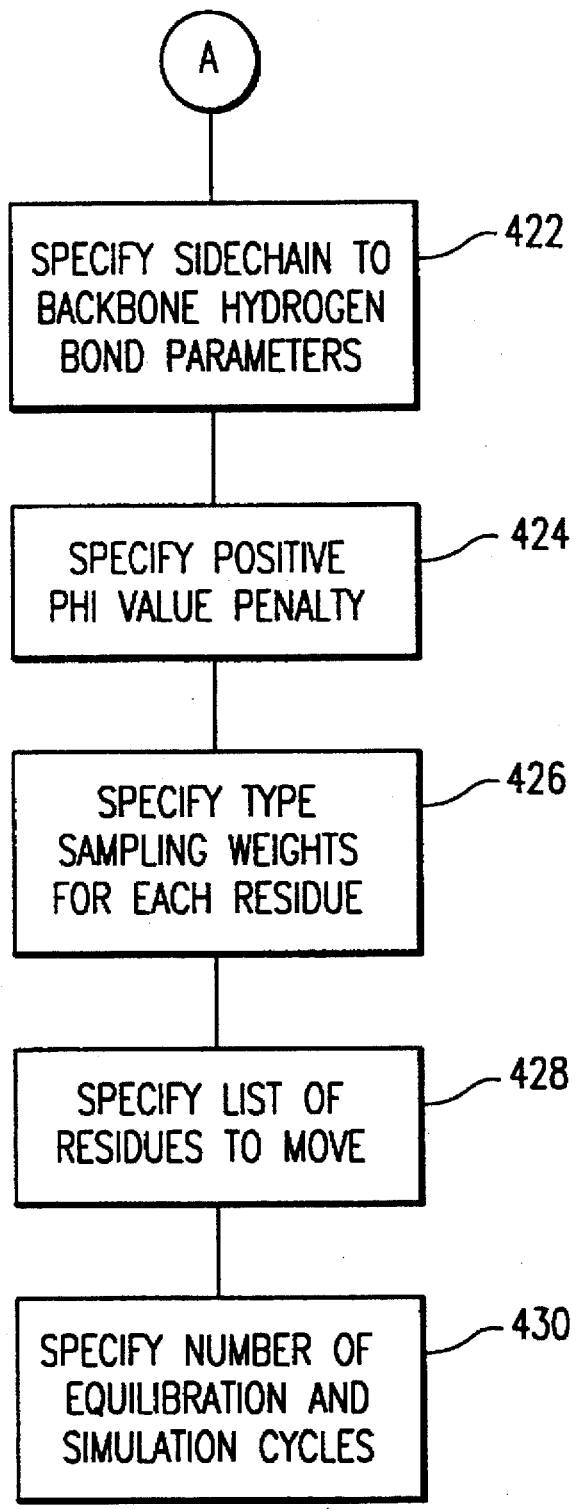

Turning to FIGS. 4a and 4b, setup step 32 includes steps 410 and 412 of storing the coordinates of the chain and the number of residues of the chain. Monte Carlo factor β is specified at step 414. The initial interval Δ, the interval increment ΔINC, and the maximum interval ΔMAX are specified at step 416. The contact energy parameters (which collectively are shown in FIGS. 2a, 2b, and 2c or set forth in the above description) are specified at step 418. The backbone hydrogen bond parameters and the side chain to backbone hydrogen bond parameters (which are set forth in the above) are specified at steps 420 and 422. The positive main chain torsion potential parameter is specified at step 424. The conformation type sampling weights for each residue position for conformation types helix, strand, turn, and coil is specified at step 426. These weights define the probability that a particular conformation type will be selected as the move for a residue. The list of residues subject to move is optionally specified at step 428. This list is an optional way to define a fragment for simulation. (In the simulation protocol described here, the move lists are sequential 50-residue fragments, as has been described.) Finally, the number of equilibration cycles and simulation cycles NCYC to be performed is specified at step 430. (The operation and use of equilibration cycles are not shown in the flow charts.)

Figure 5A:
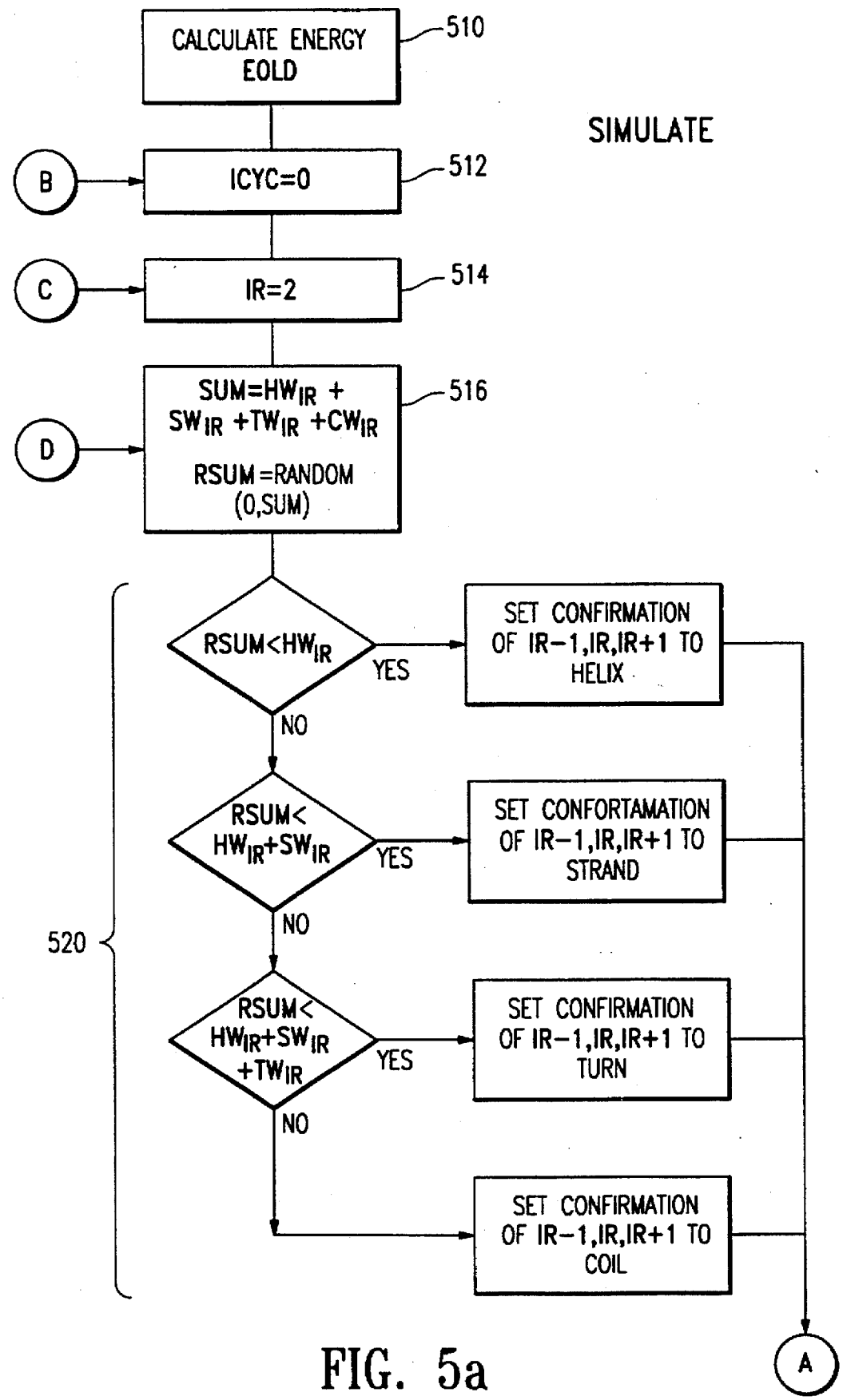
FIGS. 5a and 5b are a block diagram flow chart of a basic simulation step of an implementation of the method.
Figure 5B:
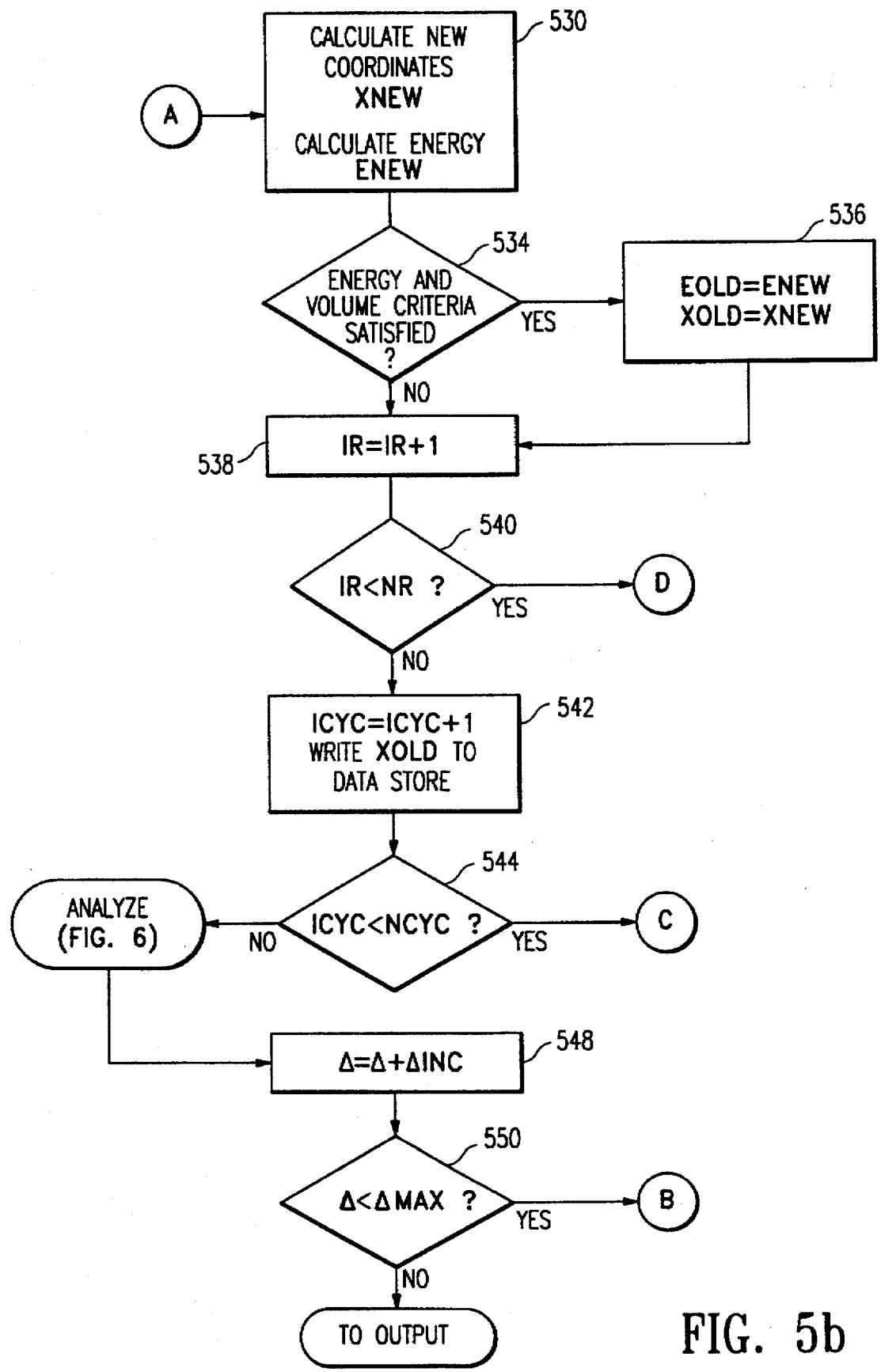

Turning to FIGS. 5a and 5b, simulation step 34 includes the step 510 of calculating U(C), steps 512 and 514 of initialing the cycle counter and residue pointer, steps 520 to randomly select a move, step 530 of calculating the chain conformation after the selected move, C*, and its energy, U(C*), and decision step 534 of checking the energy and volume criteria. (The excluded volume criterion is preferably checked first.) If the criteria are satisfied, in step 536 the conformation C is replaced by conformation C* and the energy U(C) is correspondingly replaced by U(C*). At step 538, the residue pointer is incremented to the next residue and is checked at decision step 540 for completion of the cycle. If the cycle is not completed, the process returns to step 516; otherwise it continues to step 542 of accumulating conformation C in a trial ensemble. Decision step 544 tests whether the selected number of cycles has been performed. If not, the process returns to step 514; otherwise, it continues on to the analysis steps, shown in FIG. 6.

Figure 6:
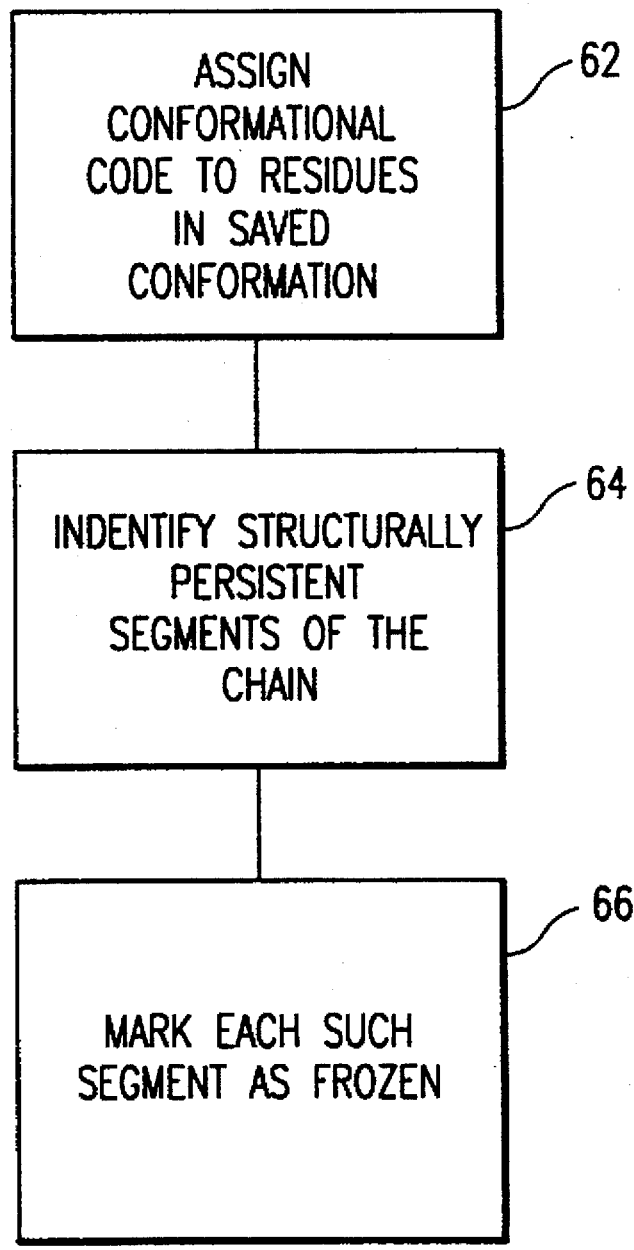
FIG. 6 is a block diagram flow chart of a basic analysis step of an implementation of the method.

Turning to FIG. 6, the analysis steps analyze the most recently accumulated trial ensemble of conformations to identify segments that are structurally persistent in the ensemble. At step 62, a conformational code is assigned to each residue of each conformation in the ensemble, identifying the region of φ, ψ-space that the residue occupies. Then, at step 64, the structurally persistent segments of the chain are identified, and at step 66, these are marked as frozen. The freezing of residues to limit the sampling of conformation types when the residues are moved (see steps 520 to 530, FIGS. 5a and 5b) is accomplished in part by resetting the type sampling weights used in step 516 and initially set in step 426 (FIG. 4b). Thus, for example, a residue frozen as a helix would have its sampling weights for other types, such as strand, set to zero.

Returning to FIG. 5b, the interval Δ is incremented at step 548 and checked against its terminal value at step 550. If the largest interval has not been processed, the process returns to step 512 for the next set of cycles. Otherwise, the last trial ensemble of conformations has been analyzed. The minimum energy structure among the last trail ensemble is accepted and output as the predicted conformation at step 38 (FIG. 3).

The preferred final conformation of the protein sequence may be output as a three-dimensional structure, such as a set of Cartesian coordinates for every atom and pseudo-atom of the amino acid sequence. However, the Sequence is preferably depicted graphically as a macromolecule on a graphical output device such as the video monitor 93 in FIG. 8a. Programs for graphically displaying such sequences are well-known in the art and include Insight II, available from BioSym of San Diego, Calif. Any suitable type of program can be used for displaying and manipulating the final protein sequence.

Preferred Apparatus for Implementation. The procedure described above is preferably implemented as a computer program stored on a storage media or device readable by a computer, for configuring and operating the computer when the storage media or device is read by the computer, the computer being operated to determine the three-dimensional structure of a protein fragment (which may be the entire protein) of known sequence in accordance with the present invention. Such a program preferably implements the following procedure:

1. generating input data for the programmed computer, including the steps of:
   (a) defining an initial conformation of a section of the protein fragment as the current conformation of such section of the protein fragment,
   (b) defining a locality window for an energy function, the locality window being a number representing a count of residues;
   (c) defining for sub-fragments of the protein fragment a constraint condition selected from a set conditions including no constraint, helix constraint, extended constraint, and same turn constraint;
2. inputting the generated input data into the programmed computer through one of the input devices;
3. computing a first energy function value for the current conformation of the current section of the protein fragment;
4. computing a second energy function value for a random next conformation of such current section of the protein fragment, where such random selection is constrained by a constraint condition associated with the current section of the protein fragment;
5. adopting as the current energy function value the next energy function value and as the current conformation the next conformation if both (1) the next energy function value is less than the current energy function value and (2) the next conformation satisfies an excluded volume criterion;
6. repeating steps (3) through (5) for a next current section of the protein fragment for a set of sections of the protein fragment;
7. adding the current conformation of the protein fragment to an ensemble of conformations stored in the data store;
8. repeating steps (3) through (7) a substantial number of times;
9. analyzing the conformations in the ensemble in the data store to define, for a segment of the protein fragment, a constraint condition selected from the set of constraint conditions;
10. repeating step (9) for a substantial number of segments of the protein fragment;
11. increasing the size of the locality window;
12. repeating steps (3) through (11) until the size of the locality window exceeds a threshold; and
13. outputting to one of the output devices a conformation of the last formed ensemble in the data store as the predicted structure.

FIG. 8a shows a perspective view of a generalized computer 90 suitable for implementing the present invention. The computer 90 includes at least one input device, which may be, for example, a keyboard 91 or a mouse 92. The computer 90 also includes at least one output device, which may be, for example, a video monitor 93. The computer also includes a processor (shown in greater detail in FIG. 8b) and at least one data store (not shown), which may be, for example, a magnetic hard disk drive, a floppy disk drive and floppy diskette, a flash memory, or even a large section of RAM memory.

Figure 8B:
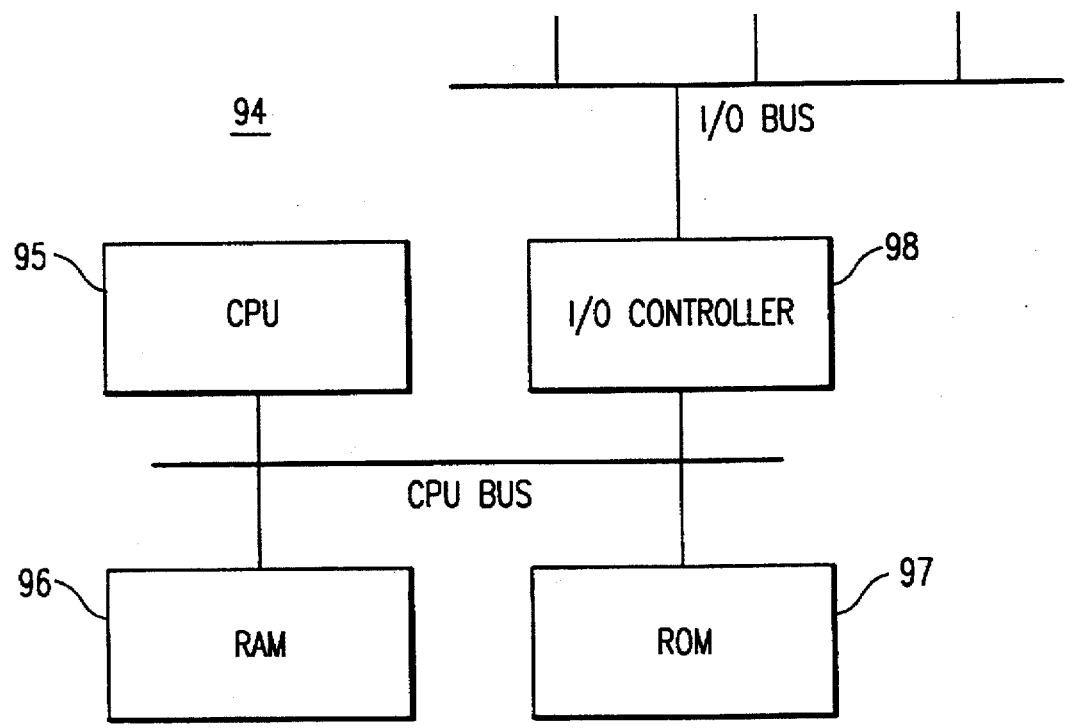

FIG. 8b shows a block diagram of the processor 94 of the computer 90. The processor preferably includes a CPU 95, a RAM 96, a ROM 97, and an I/O Controller 98 coupled by a CPU bus. External devices may be coupled to the processor 94 through an I/O bus coupled to the I/O Controller 98. Processors such as processor 94 are well-known in the art.

While of great interest for its ability to predict three-dimensional protein structures, the method may be used for other purposes as well. For example, three-dimensional structures may be predicted for use in protein design, to aid in screening and development of diagnostic and therapeutic protein fragments as in rational drug design, to search for structural analogs of known protein structures, or to aid in an analysis of biological function and activity. Also, the method may be used to predict protein secondary structures and protein subsecondary structures from amino acid sequences alone, and to predict those regions of a protein molecule that are on the outside and those that are on the inside.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

What is claimed is:

1. A computer-implemented method for predicting the three-dimensional structure of a protein fragment, implemented on a programmed computer, the method comprising:
   (a) creating in the computer an ensemble of conformations for the protein fragment satisfying a localized energy condition using a random selection strategy;
   (b) identifying, by operation of a program, persistently stable segments of the fragment in the ensemble;
   (c) creating in the computer a next ensemble of conformations satisfying a localized energy condition with a larger locality window and constrained a) not to change the conformation types of persistently stable segments and b) by a constraint condition associated with the current segment of the protein fragment;
   (d) identifying, by operation of a program, further persistently stable segments of the fragment in the next ensemble;
   (e) repeating steps (c) and (d) for increasingly large locality windows; and
   (f) outputting from the computer as the predicted three-dimensional structure a conformation in the last-formed ensemble.

2. The method of claim 1 wherein the random selection strategy is a Monte Carlo strategy.

3. The method of claim 1 wherein the localized energy condition is selected to satisfy a Boltzmann distribution in the ensemble.

4. The method of claim 1 wherein persistently stable segments have conformation types selected from types including helix and coil.

5. The method of claim 1 wherein the protein is a globular protein.

6. The method of claim 1 wherein the repetition of steps (c) and (d) in step (e) is performed at least about 5000 times.

7. The method of claim 1 further comprising a step of repeating steps (c) and (d) to achieve equilibration before performing step (e).

8. The method of claim 1 wherein the side chains of the protein fragment are represented in a simplified form using pseudo-atoms.

9. The method of claim 1 wherein the localized energy condition is that a next conformation have an energy value typically less than a current conformation energy value and wherein the energy value of a conformation includes a sum of a contact energy, a hydrogen bonding potential, and a main chain torsional potential.

10. A computer-assisted method for predicting the 3-dimensional structure of a protein fragment, using a programmed computer comprising a processor, a data store, at least one input device, and at least one output device, the method comprising:
   (a) generating input data for the programmed computer, including the step of defining an initial conformation of a section of the protein fragment as the current conformation of such section of the protein fragment;
   (b) inputting the generated input data into the programmed computer through one of the input devices;
   (c) computing a first energy function value for the current conformation of the current section of the protein fragment;
   (d) computing a second energy function value for a random next conformation of such current section of the protein fragment, where such random selection is constrained by a constraint condition associated with the current section of the protein fragment;
   (e) adopting as the current energy function value the next energy function value and as the current conformation the next conformation if both (1) the next energy function value is less than the current energy function value and (2) the next conformation satisfies an excluded volume criterion;
   (f) repeating steps (c) through (e) for a next current section of the protein fragment for a set of sections of the protein fragment;
   (g) adding the current conformation of the protein fragment to an ensemble of conformations stored in the data store;
   (h) repeating steps (c) through (g) a substantial number of times;
   (i) analyzing the conformations in the ensemble in the data store to define, for a segment of the protein fragment, a constraint condition selected from a set of pre-defined constraint conditions;
   (j) repeating step (i) for a substantial number of segments of the protein fragment;
   (k) outputting to one of the output devices a conformation of the last formed ensemble in the data store as the predicted structure.

11. A computer-assisted method for predicting the 3-dimensional structure of a protein fragment, using a programmed computer comprising a processor, a data store, at least one input device, and at least one output device, the method comprising:
   (a) generating input data for the programmed computer, including the steps of:
      (1) defining an initial conformation of a section of the protein fragment as the current conformation of such section of the protein fragment, (2) defining a locality window for an energy function, the locality window being a number representing a count of residues, and (3) defining for sub-fragments of the protein fragment a constraint condition selected from a set of constraint conditions including a) no constraint, b) helix constraint, c) extended constraint, and d) same turn constraint;

(b) inputting the generated input data into the programmed computer through one of the input devices;

(c) computing a first energy function value for the current conformation of the current section of the protein fragment;

(d) computing a second energy function value for a random next conformation of such current section of the protein fragment, where such random selection is constrained by the constraint condition associated with the current section of the protein fragment;

(e) adopting as the current energy function value the next energy function value and as the current conformation the next conformation if both (1) the next energy function value is approximately less than the current energy function value and (2) the next conformation does not create steric overlap;

(f) repeating steps (c) through (e) for a next current section of the protein fragment for a set of sections of the protein fragment;

(g) adding the current conformation of the protein fragment to an ensemble of conformations stored in the data store;

(h) repeating steps (c) through (g) a substantial number of times;

(i) analyzing the conformations in the data store to define, for a segment of the protein fragment, a constraint condition selected from the set of constraint conditions;

(j) repeating step (i) for a substantial number of segments of the protein fragment;

(k) increasing the size of the locality window;

(l) repeating steps (c) through (k) until the size of the locality window exceeds a threshold, whereby hierarchical accretion of constraint conformation is realized; and (m) outputting to one of the output devices a conformation of the last formed ensemble in the data store as the predicted structure.

* * * * *

UNITED STATES PATENT AND TRADEMARK OFFICE
CERTIFICATE OF CORRECTION

PATENT NO.  : 5,680,319

DATED       : 10/21/97

INVENTOR(S) : George D. Rose and Rajgopal Srinivasan

It is certified that error appears in the above-identified patent and that said Letters Patent is hereby corrected as shown below:

ON THE TITLE PAGE:

Item [75] Inventors: Inventor Srinivasan's first name is misspelled and should be corrected to --Rajgopal--.

Signed and Sealed this

Fourth Day of August, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   : 5,680,319
DATED        : October 21, 1997
INVENTOR(S)  : George D. Rose and Rajgopal Srinivasan It is certified that error appears in the above-identified patent and that said Letters Patent is hereby corrected as shown below:

<u>Column 1,</u>
Please insert the following:

-- This invention was made with Government support under EY10852 awarded by the PHS. The Government has certain rights in the invention. --

Signed and Sealed this

Third Day of December, 2002

JAMES E. ROGAN
*Director of the United States Patent and Trademark Office*